(12) United States Patent
Cole et al.

(10) Patent No.: US 9,921,144 B2
(45) Date of Patent: Mar. 20, 2018

(54) PARTICULATE MATTER DETECTOR

(71) Applicant: Honeywell International Inc., Morris Plains, NJ (US)

(72) Inventors: Barrett E. Cole, Bloomington, MN (US); Robert P. Costello, Roseville, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/196,808

(22) Filed: Jun. 29, 2016

(65) Prior Publication Data
US 2018/0003612 A1    Jan. 4, 2018

(51) Int. Cl.
| G01N 21/00 | (2006.01) |
| G01N 15/14 | (2006.01) |
| G01N 15/06 | (2006.01) |
| G01N 15/10 | (2006.01) |

(52) U.S. Cl.
CPC ......... *G01N 15/1434* (2013.01); *G01N 15/06* (2013.01); *G01N 2015/1043* (2013.01)

(58) Field of Classification Search
CPC ........... G01N 15/1459; G01N 15/1434; G01N 15/1436; G01N 2021/6469; G01N 21/49; G01N 2015/1452; G01N 2015/149; G01N 15/0205; G01N 2015/1493; G01N 21/47; G01N 21/64; G01N 21/645; G01N 15/14
See application file for complete search history.

(56) References Cited

U.S. PATENT DOCUMENTS

| 3,535,531 | A | 10/1970 | Neitzel | |
| 4,523,841 | A | 6/1985 | Brunsting | |
| 5,024,526 | A | 6/1991 | Von Redwitz | |
| 6,636,308 | B1* | 10/2003 | Tsutsui | G01N 21/474 |
| | | | | 356/336 |
| 7,126,687 | B2 | 10/2006 | Hill et al. | |
| 7,999,936 | B1 | 8/2011 | Li et al. | |
| 8,358,411 | B2* | 1/2013 | Babico | G01N 15/1459 |
| | | | | 356/335 |
| 2003/0223063 | A1* | 12/2003 | Hill | G01N 21/64 |
| | | | | 356/340 |
| 2007/0285661 | A1* | 12/2007 | Saunders | G01N 15/1459 |
| | | | | 356/336 |

OTHER PUBLICATIONS

Fernandes, et al., "Simultaneous forward- and backward-hemisphere elastic-light-scattering patterns of respirable-size aerosols", Optics Letters, Oct. 15, 2006, 3 pp, vol. 31, No. 20.
Extended Search Report from related European Patent Application No. 17178194.1, dated Sep. 11, 2017, 9 pages.

* cited by examiner

*Primary Examiner* — Michael P Stafira
(74) *Attorney, Agent, or Firm* — Brooks, Cameron & Huebsch, PLLC (57) ABSTRACT

Devices and methods for detecting particulate matter are described herein. One device includes a laser, a reflector, an ellipsoidal reflector, and a detector, wherein the laser is configured to emit a beam, the reflector is configured to reflect the beam toward the ellipsoidal reflector, and the ellipsoidal reflector has a first focal region located on a path of the reflected beam, and a second focal region located at a surface of the detector.

20 Claims, 7 Drawing Sheets

PARTICULATE MATTER DETECTOR

TECHNICAL FIELD

The present disclosure relates to devices and methods for detecting particulate matter.

BACKGROUND

Airborne particulate matter poses a variety of health and environmental issues. Soot, for instance, caused by combustion (e.g., burning coal, wood, cigarettes, and/or automotive exhaust) may be the primary contaminant in some regions in that it may account for most of the particulate mass present in the air. Despite this, however, individual soot particles can often be relatively small. For instance, soot particles may be smaller than one micron in diameter.

Previous approaches to detecting particulate matter may count particles as they scatter laser light. The scattered light from each particle may be counted by a detector as the particles pass through the laser beam near the detector. However, these approaches may rely on precise airflow control to measure count rate in order to determine the particle number density. Moreover, the 90-degree scattered light detected in previous approaches may only be strong enough such that only particles that are about a micron in diameter or larger are counted. In these approaches, the Mie scattering of smaller particles may be too weak to be detected.

In order to estimate the true particle air mass, these previous approaches may use the count of particles multiplied by a scale (or correction) factor. However, because the actual air mass is so undercounted when counting particles, the scale factors used may need to be large (e.g., on the order of twenty times the counted particle mass). Thus, in order to determine an air mass of micrograms per cubic meter, previous approaches may rely on a scale factor that is undesirably large.

DETAILED DESCRIPTION

Devices and methods for detecting particulate matter are described herein. For example, one or more embodiments can include a laser, a reflector, an ellipsoidal reflector, and a detector, wherein the laser is configured to emit a beam, the reflector is configured to reflect the beam toward the ellipsoidal reflector, and the ellipsoidal reflector has a first focal region located on a path of the reflected beam, and a second focal region located at a surface of the detector.

Embodiments of the present disclosure can detect particulate matter (hereinafter referred to as "soot," "particles," or "soot particles") using forward scatter light as a signal and can thus be more sensitive to small particles than previous approaches. When considered in terms of scattered light per unit mass, forward scattering of many more small particles can provide a stronger signal compared to a few large particles which are counted in previous approaches. Embodiments of the present disclosure can leverage the benefits of forward scatter light by collecting that light from a region in space where small particles exist in the ambient air.

In some embodiments, a laser can emit a beam, which can be directed towards a reflector (e.g., mirror). In some embodiments, the reflector can be ellipsoidal; in some embodiments, the reflector can be substantially spherical. The reflector is herein referred to as "ellipsoidal reflector," though, as noted, embodiments of the present disclosure are not so limited.

In some embodiments the laser can emit the beam directly towards the ellipsoidal reflector. In some embodiments, the emitted beam can be reflected by a reflector configured to direct the beam towards the ellipsoidal reflector. As the beam passes through a focal region (e.g., a focus) of the ellipsoidal reflector, soot particles can scatter the laser light. The scattered laser light can be reflected by the ellipsoidal mirror back to a detector. The detector can measure an intensity of the scattered light (e.g., "cloud intensity") to determine air mass. It is noted that the measured intensity is proportional to the airborne particulate mass. In some embodiments, particles can additionally be counted. Such embodiments may be beneficial in cases where the air is dominated by few, large particles rather than smaller particles, for instance.

Previous approaches that rely on counting particles (e.g., 90-degree scattering dust sensors) may count particles that are greater than 0.5 microns in diameter (or greater than 0.8 microns in some cases). However, most air mass may be comprised of particles between 0.1 and 0.6 microns in diameter. In addition, numerically, most particles in ambient air may fall between 0.1 and 0.4 microns in diameter. Thus, previous approaches may undercount the actual particulate content and rely on a correction factor (e.g., 6× to 20×) to generate a true fine particle pollution (PM2.5) mass value.

Embodiments of the present disclosure can reduce the inaccuracies associated with large correction factors and can reduce costs associated with precise airflow control seen in previous approaches. Moreover, embodiments herein may be manufactured at relatively low cost. For instance, the use of lenses and/or specialized optical equipment requiring intensive alignment or calibration may be avoided.

In some embodiments, a number of fixed baffles can be positioned to block scattered light that was not scattered in the focal region of the ellipsoidal reflector. Accordingly, the detector can be prevented from receiving duplicative signals and can sample a finite region of ambient air.

For instance, while particles may scatter light along an entire path of the laser beam, the use of the ellipsoidal reflector in conjunction with the baffles can allow the imaging of a small region (e.g., a focal region) of the pathlength. The detector can be placed at the other focus of the ellipsoidal reflector. Light that is scattered off of particles in other regions (not in the focal region) can reflect off of the ellipsoidal mirror at angles that do not focus the light onto the detector but instead reflect it onto one or more baffles that block and/or absorb the light.

By particular sizing of the baffle(s) and/or the ellipsoidal reflector, embodiments of the present disclosure can allow the detector to receive light that is scattered off particles within a narrow forward scatter range. For instance, the ellipsoidal reflector can reflect scattered light over a range of 20 to 35 degrees. A smaller forward angle may increase the signal, for instance. In some embodiments, an angle range is selected that allows the detection of particles in the range of 0.2 to 0.7 microns while providing a sufficiently large signal to detect scattered radiation at 25 microgram per cubic meter air loadings.

Embodiments of the present disclosure can be used as a monitor in air cleaners, for instance, to demonstrate that the air cleaner is functioning properly and/or provide a measure of air quality. Embodiments of the present disclosure can be used to control the fan speed of an air cleaner so that when air is highly contaminated, the fan runs at a higher throughput speed. Embodiments of the present disclosure can be used as a PM2.5 air quality monitor at a lower cost than previous approaches.

The present disclosure is not limited to particular devices or methods, which may vary. The terminology used herein is for the purpose of describing particular embodiments, and is not intended to be limiting. As used herein, the singular forms "a", "an", and "the" include singular and plural referents unless the content clearly dictates otherwise. Furthermore, the words "can" and "may" are used throughout this application in a permissive sense (i.e., having the potential to, being able to), not in a mandatory sense (i.e., must). The term "include," and derivations thereof, mean "including, but not limited to."

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

Figure 1:
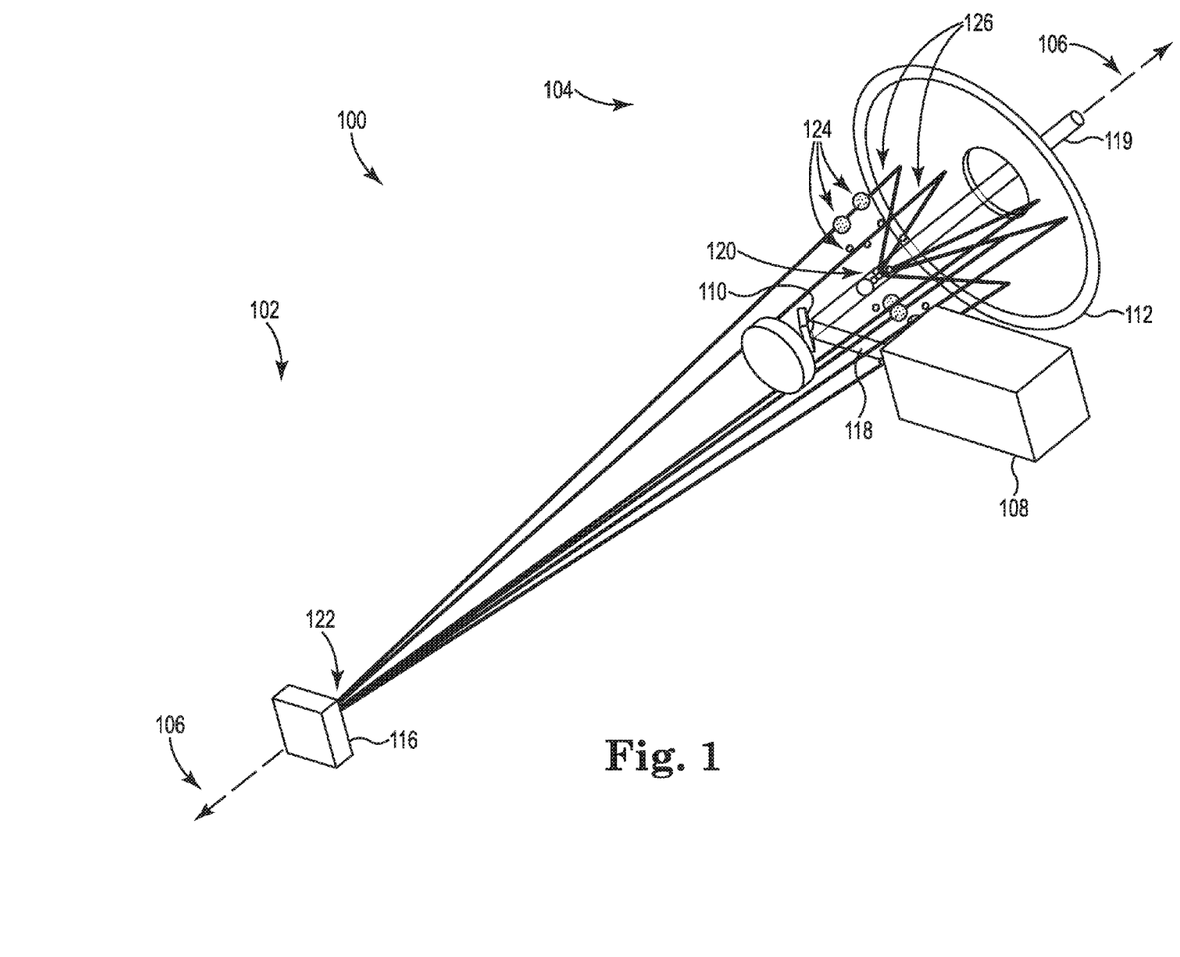
FIG. 1 illustrates a perspective view of a device for detecting particulate matter in accordance with one or more embodiments of the present disclosure.

FIG. 1 illustrates a perspective view of a device 100 for detecting particulate matter in accordance with one or more embodiments of the present disclosure. As shown in FIG. 1, the device 100 includes a first end 102 and a second end 104 opposing the first end 102. An optical axis 106 passes through the first end 102 and the second end 104.

The device 100 includes a laser 108. The laser 108 can emit a beam of light 118 and can be positioned such that the beam 118 is emitted substantially perpendicular to the optical axis 106 (as shown in FIG. 1). In some embodiments, the beam 108 is at a 90-degree angle relative to the optical axis 106. The laser 108 is not intended to be limited to a particular type, make, and/or model by embodiments herein. It is to be understood that a wavelength of the beam 118 may affect scattering and/or measured intensity. For instance, a blue light may provide increased scattering but may provide reduced intensity.

The device 100 includes a reflector 110. In some embodiments, the reflector 110 can be a mirror. In some embodiments, the reflector 110 can be a beamsplitter. As shown in the example illustrated in FIG. 1, the reflector 110 can be angled with respect to the optical axis 106. In some embodiments, the angle can be substantially 45 degrees with respect to the optical axis 106. The angle can be selected based on the positioning and/or angle of the laser 108, for instance. The reflector 110 can reflect the beam 118 such that it travels along the optical axis 106 toward the second end 104 as a reflected beam 119.

As shown in FIG. 1, the device 100 includes an ellipsoidal reflector (e.g., mirror) 112 substantially centered on the optical axis 106 at the second end 104. The ellipsoidal reflector 112 can be an ellipsoidal and/or elliptical mirror, for instance, that has two foci. As shown in FIG. 1, a first focus (sometimes referred to herein as a "focal region") 120 is located between the reflector 110 and the ellipsoidal reflector 112. A second focal region 122 is located proximal to a detector 116 (discussed below). The ellipsoidal reflector 112 can be formed by stamping a metal foil, for instance, using an ellipsoidal stamp.

As shown in FIG. 1, the ellipsoidal reflector 112 can have an opening therethrough. In some embodiments, the opening is substantially centered in the ellipsoidal reflector 112. The opening can allow the reflected beam 119 to pass through the ellipsoidal reflector 112. In some embodiments, the beam can enter a beam dump (e.g., such as that illustrated in FIG. 4, for instance).

The first focal region 120 can be, as shown in FIG. 1, located on a path of the reflected beam 119. Airborne particles 124 can travel through the first focal region 120. The particles 124 can scatter the light of the reflected beam 119. The scattered light 126 (e.g., forward scattered light) can reflect off of the ellipsoidal reflector 112 and travel towards the first end 102 to converge at the second focal region 122.

The device 100 can include a detector 116. As shown in FIG. 1, the detector 116 can be positioned at the second focal region 122 and can be substantially perpendicular to the optical axis 106. In some embodiments, a surface (e.g., a detecting surface) of the detector 116 can be positioned at the second focal region 122 (e.g., proximal to the second focal region 122). The detector 116 can be a light sensor, for instance. In some embodiments, the detector 116 can include a photodiode (e.g., a silicon photodiode). The detector 116 can receive the scattered light 126 and convert the scattered light 126 into a signal (e.g., an analog signal) based on an intensity (luminosity and/or luminous intensity) of the scattered light 126. The strength of the signal may be proportional to a mass of particulate matter in the air.

Figure 2:
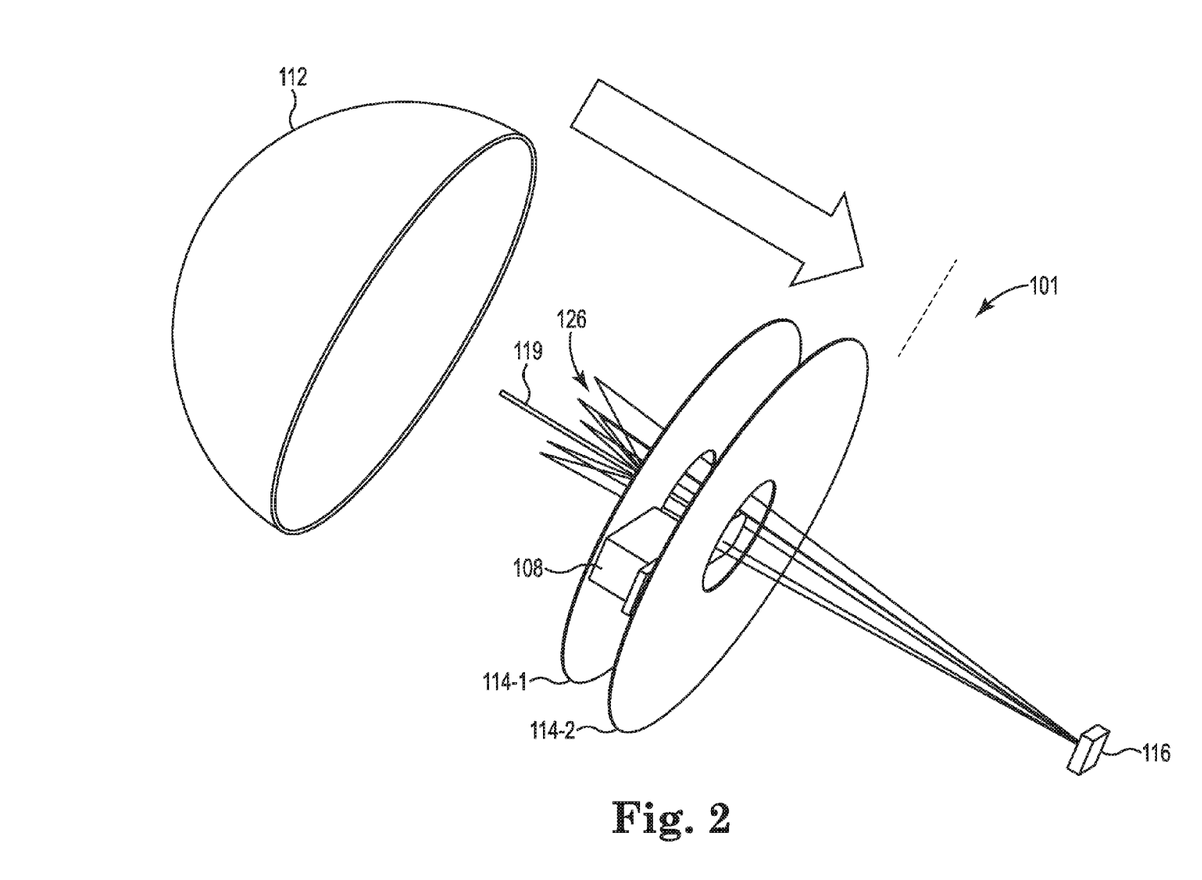
FIG. 2 illustrates a partially exploded view of a device for detecting particulate matter in accordance with one or more embodiments of the present disclosure.

FIG. 2 illustrates a partially exploded view of a device 101 for detecting particulate matter in accordance with one or more embodiments of the present disclosure. As shown in the example illustrated in FIG. 2, devices in accordance with the present disclosure can include a baffle 114-1 and a baffle 114-2 (cumulatively referred to herein as "baffles 114"). Though two baffles are shown in FIG. 2, embodiments herein are not limited to a particular number of baffles. The baffles 114 can be positioned to block the scattered light that was not scattered in the first focal region 120 of the ellipsoidal reflector 112 (i.e., block scattered light that is not the scattered light 126). Accordingly, the detector 116 can be prevented from receiving duplicative signals and can sample a finite region of ambient air.

By particular sizing of the baffle(s) 114 and/or the ellipsoidal reflector 112, embodiments of the present disclosure can allow the detector 116 to receive light that is scattered off particles within a narrow forward scatter range. For instance, the ellipsoidal reflector 112 can reflect scattered light over a range of 20 to 35 degrees. A smaller forward angle may increase the signal, for instance. In some embodiments, an angle range is selected that allows the detection of particles in the range of 0.2 to 0.7 microns while providing a sufficiently large signal to detect scattered radiation at 25 microgram per cubic meter air loadings.

As seen in the example illustrated in FIG. 2, in some embodiments, the ellipsoidal reflector 112 can be pulled away from the laser 108, the baffles 114, and the detector 116. In some embodiments, the ellipsoidal reflector 112 can be a portion of a first assembly. The first assembly can include, for instance, the ellipsoidal reflector 112, a beam dump (discussed further below), and a flow sheath (discussed further below), if applicable.

In some embodiments, the laser 108, the detector 116, the reflector 110 (obscured by the baffles 114 in FIG. 2), and the baffles 114 can be a portion of a second assembly. In some embodiments, the first and second assemblies may include a respective portion of a housing to which their constituent components can be affixed. In some embodiments, the first and second assemblies can be secured to one another. In some embodiments, the first and second assemblies can slide together along the optical axis using a tongue and groove joint or sliding dovetail joint. In some embodiments, securing the first assembly and the second assembly to one another aligns the optical components therein.

Figure 3:
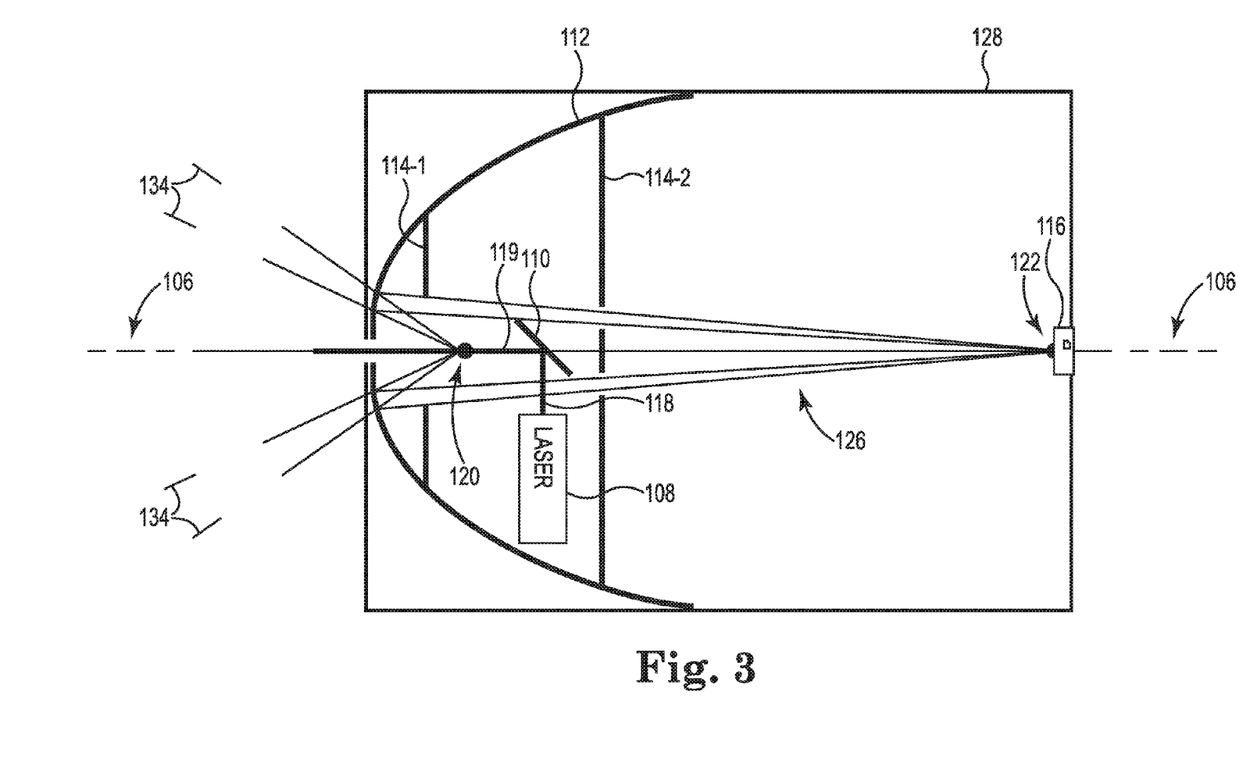
FIG. 3 illustrates a top view of a device for detecting particulate matter in accordance with one or more embodiments of the present disclosure.

FIG. 3 illustrates a top view of a device for detecting particulate matter in accordance with one or more embodiments of the present disclosure. As seen in FIG. 3, the scattered light 126 can be reflected by the ellipsoidal reflector 112 and received by the detector 116 in a particular angle range 134. In some embodiments, the angle range 134 can be between 25 degrees and 35 degrees (i.e., degrees from the optical axis.

As seen in FIG. 3, the device includes a housing 128. In some embodiments, the housing 128 can be opaque to ambient light. In some embodiments, the housing can include one or more materials that absorb light (or a particular wavelength of light). The housing 128 can include at least one surface defining an opening that allows ambient air to enter the housing.

Figure 4:
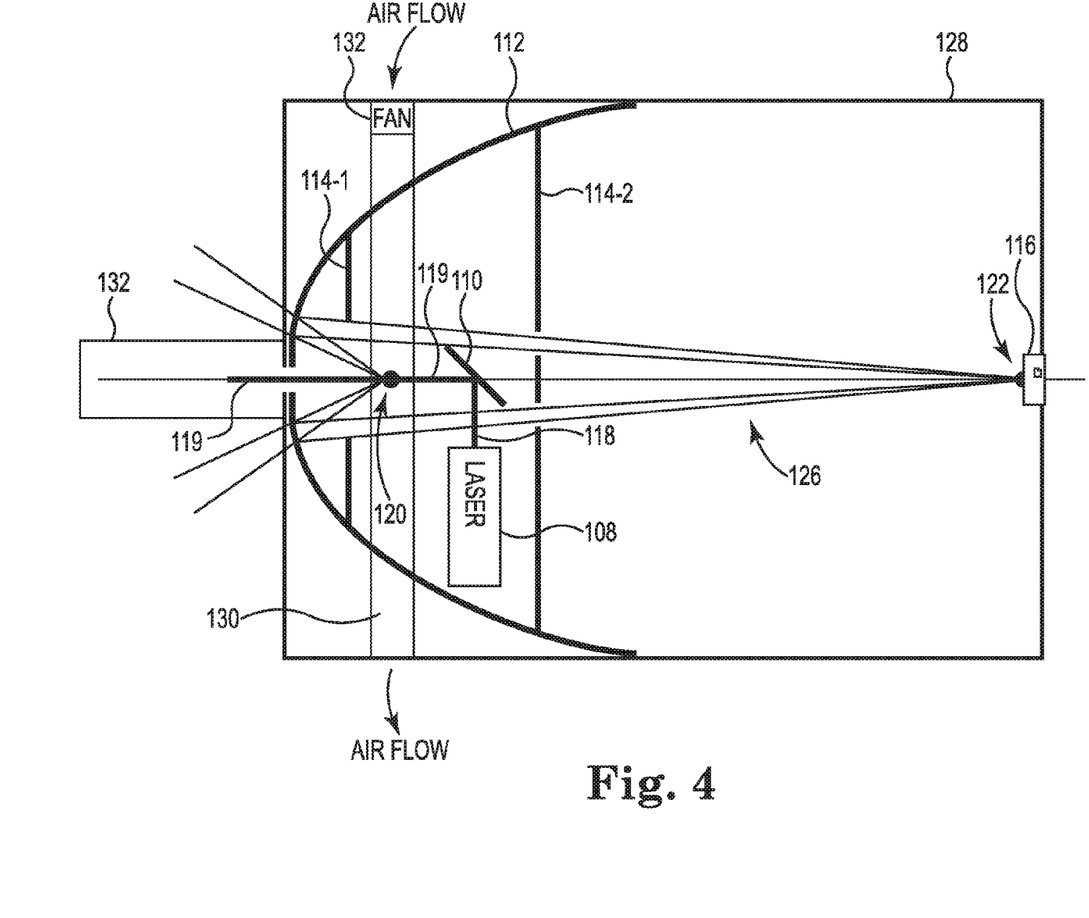
FIG. 4 illustrates a top view of a device for detecting particulate matter in accordance with one or more embodiments of the present disclosure.

FIG. 4 illustrates a top view of a device for detecting particulate matter in accordance with one or more embodiments of the present disclosure. As shown in FIG. 4, particulate matter detectors in accordance with the present disclosure can include a beam dump 132. The beam dump 132 is a device designed to absorb the energy of photons or other particles within an energetic beam (e.g., the reflected beam 119).

The example illustrated in FIG. 4 includes a flow sheath 130. In some embodiments, a flow sheath 130 can be added to separate the airborne dust (and other contaminants) from components such as the ellipsoid mirror 112, the laser 108, and/or the reflector 110, for instance. The flow sheath 130 can be a circular tube, for instance. In some embodiments, the flow sheath 130 can be a rectangular tube. The flow sheath 130 can be made of class, in some embodiments. Openings in the flow sheath 130 can be provided such that the reflected beam 119 and/or the scattered light 126 pass by the flow sheath 130 rather than through it, which could alter the properties of the light.

In some embodiments, the device can include a fan 132 configured to propel air, and thus airborne soot, through the flow sheath 130. The fan 132 can be controlled by a controller and/or a computing device, for instance, which may be a same device used to determine the intensity of the scattered light 126, in some embodiments.

Figure 5:
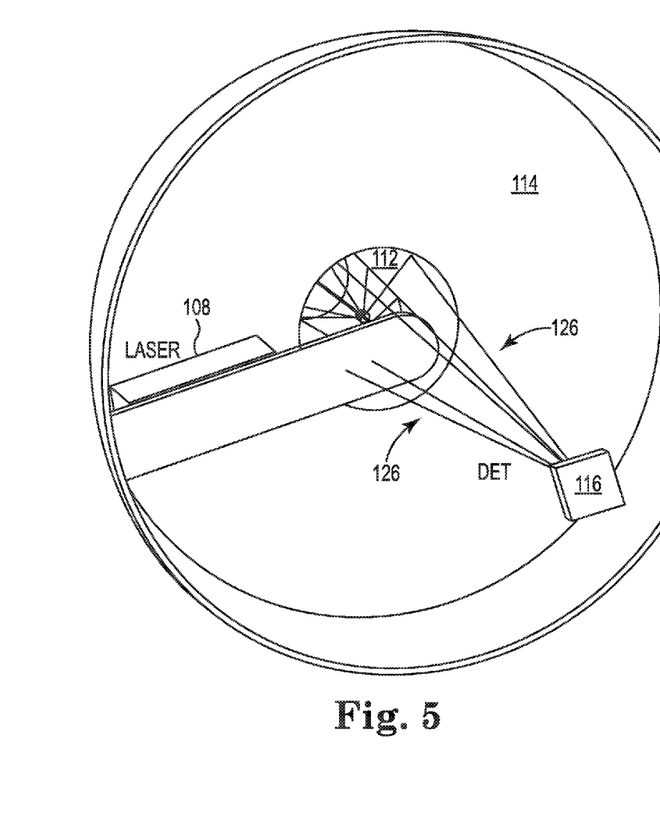
FIG. 5 illustrates another perspective view of a device for detecting particulate matter in accordance with one or more embodiments of the present disclosure.

FIG. 5 illustrates another perspective view of a device for detecting particulate matter in accordance with one or more embodiments of the present disclosure. The scattered light 126 can be seen reflecting off of the ellipsoidal reflector 112, past the baffle 114, and back towards the detector 116.

Figure 6:
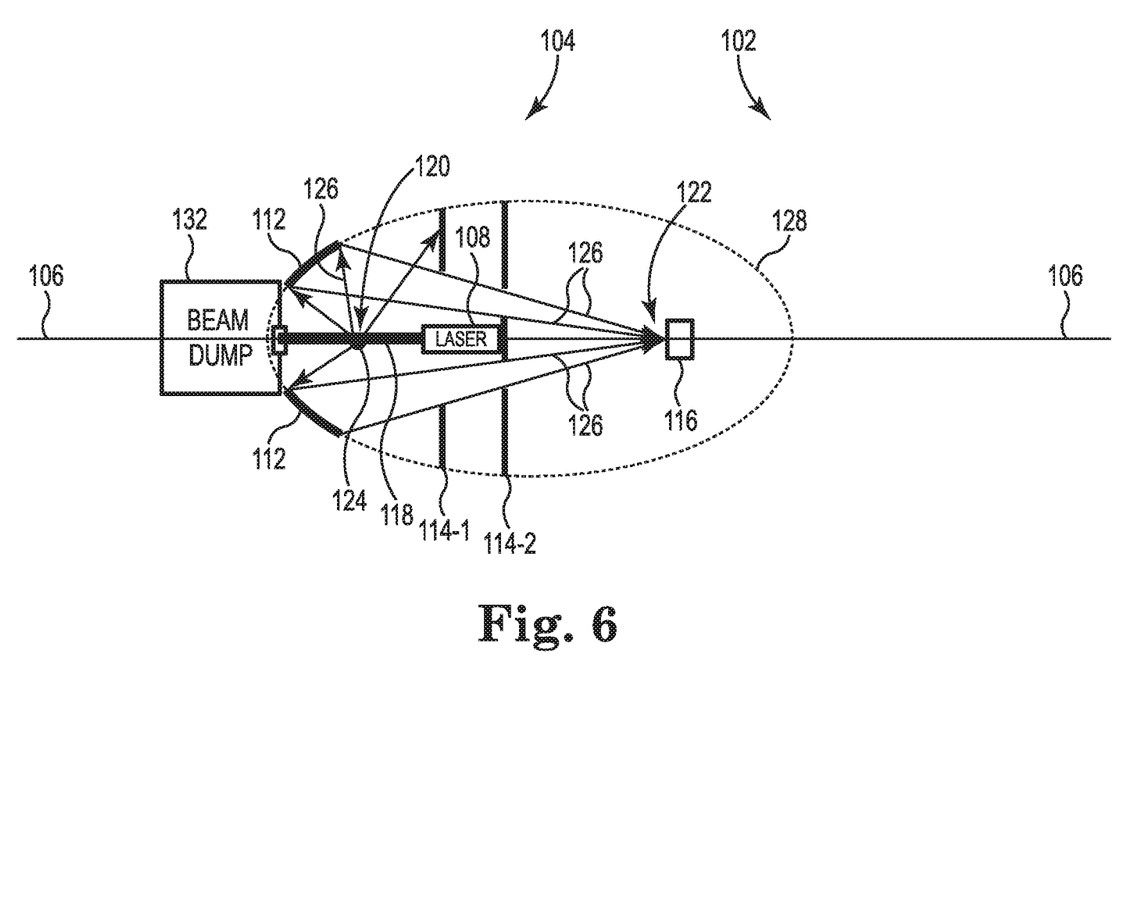
FIG. 6 illustrates a top view of a device for detecting particulate matter in accordance with one or more embodiments of the present disclosure.

FIG. 6 illustrates a top view of a device for detecting particulate matter in accordance with one or more embodiments of the present disclosure. As shown in FIG. 6, the device includes a first end 102 and a second end 104 opposing the first end 102. An optical axis 106 passes through the first end 102 and the second end 104.

The device includes a laser 108. The laser 108 can emit a beam of light 118 and can be positioned such that the beam 118 is emitted substantially parallel to the optical axis 106 (as shown in FIG. 6). The laser 108 is not intended to be limited to a particular type, make, and/or model by embodiments herein. It is to be understood that a wavelength of the beam 118 may affect scattering and/or measured intensity. For instance, a blue light may provide increased scattering but may provide reduced intensity.

The device illustrated in FIG. 6 does not include a reflector as described above. Rather, the laser 108 can emit the beam 118 such that it travels along the optical axis 106 toward the second end 104.

As shown in FIG. 6, the device includes a reflector (e.g., mirror) 112 substantially centered on the optical axis 106 at the second end 104. In some embodiments, the reflector 112 can be ellipsoidal. In some embodiments, the reflector can be spherical. In FIG. 6, the reflector is referred to as "ellipsoidal," though, as previously discussed, embodiments of the present disclosure are not so limited. The ellipsoidal reflector 112 can have two foci. As shown in FIG. 6, a first focus (sometimes referred to herein as a "focal region") 120 is located between the laser 108 and the ellipsoidal reflector 112. A second focal region 122 is located proximal to a detector 116 (discussed below). The ellipsoidal reflector 112 can be formed by stamping a metal foil, for instance, using an ellipsoidal stamp.

As shown in FIG. 6, the ellipsoidal reflector 112 can have an opening therethrough. In some embodiments, the opening is substantially centered in the ellipsoidal reflector 112. The opening can allow the beam 118 to pass through the ellipsoidal reflector 112. As shown in FIG. 6, the beam 118 can enter a beam dump 132 (e.g., such as that illustrated in FIG. 4, for instance).

The first focal region 120 can be, as shown in FIG. 6, located on a path of the beam 118. Airborne particles 124 can travel through the first focal region 120. The particles 124 can scatter the light of the beam 118. The scattered light 126 (e.g., forward scattered light) can reflect off of the ellipsoidal reflector 112 and travel towards the first end 102 to converge at the second focal region 122.

The device can include a detector 116. As shown in FIG. 6, the detector 116 can be positioned at the second focal region 122 and can be substantially perpendicular to the optical axis 106. In some embodiments, a surface (e.g., a detecting surface) of the detector 116 can be positioned at the second focal region 122 (e.g., proximal to the second focal region 122). The detector 116 can be a light sensor, for instance. In some embodiments, the detector 116 can include a photodiode (e.g., a silicon photodiode). The detector 116 can receive the scattered light 126 and convert the scattered light 126 into a signal (e.g., an analog signal) based on an intensity (luminosity and/or luminous intensity) of the scattered light 126. The strength of the signal may be proportional to a mass of particulate matter in the air.

As shown in the example illustrated in FIG. 6, devices in accordance with the present disclosure can include a baffle 114-1 and a baffle 114-2 (cumulatively referred to herein as "baffles 114"). Though two baffles are shown in FIG. 6, embodiments herein are not limited to a particular number of baffles. The baffles 114 can be positioned to block the scattered light that was not scattered in the first focal region 120 of the ellipsoidal reflector 112 (i.e., block scattered light that is not the scattered light 126). Accordingly, the detector 116 can be prevented from receiving duplicative signals and can sample a finite region of ambient air.

By particular sizing of the baffle(s) 114 and/or the ellipsoidal reflector 112, embodiments of the present disclosure can allow the detector 116 to receive light that is scattered off particles within a narrow forward scatter range. For instance, the ellipsoidal reflector 112 can reflect scattered light over a range of 20 to 35 degrees. A smaller forward angle may increase the signal, for instance. In some embodiments, an angle range is selected that allows the detection of particles in the range of 0.2 to 0.7 microns while providing a sufficiently large signal to detect scattered radiation at 25 microgram per cubic meter air loadings.

Figure 7:
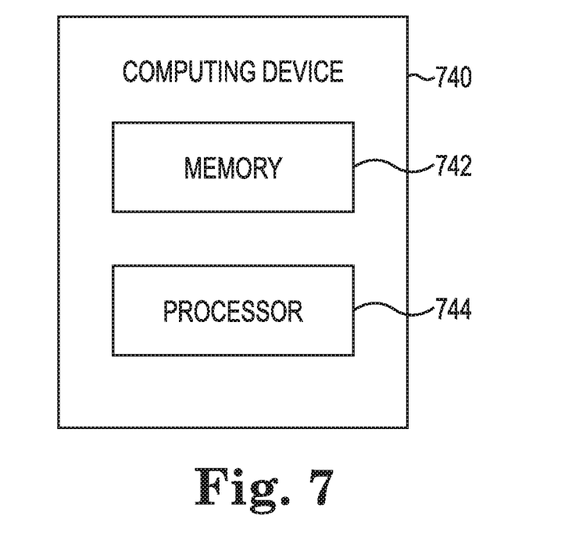
FIG. 7 illustrates a computing device for detecting particulate matter in accordance with one or more embodiments of the present disclosure.

FIG. 7 illustrates a computing device 740 for detecting particulate matter in accordance with one or more embodiments of the present disclosure. The computing device 740 can be, for example, a handheld network analyzer, laptop computer, desktop computer, or a mobile device (e.g., a mobile phone, a personal digital assistant, etc.), among other types of computing devices.

As shown in FIG. 7, the computing device 740 includes a memory 742 and a processor 744 coupled to memory 742. The memory 742 can be any type of storage medium that can be accessed by processor 744 to perform various examples of the present disclosure. For example, the memory 742 can be a non-transitory computer readable medium having computer readable instructions (e.g., computer program instructions) stored thereon that are executable by processor the 744 to determine a mass concentration of soot based on a luminous intensity of light received by a detector.

The memory 742 can be volatile or nonvolatile memory. The memory 742 can also be removable (e.g., portable) memory, or non-removable (e.g., internal) memory. For example, the memory 742 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical disk storage, and/or a magnetic medium such as magnetic cassettes, tapes, or disks, among other types of memory.

Further, although the memory 742 is illustrated as being located in the computing device 740, embodiments of the present disclosure are not so limited. For example, the memory 742 can also be located internal to another computing resource (e.g., enabling computer readable instructions to be downloaded over the Internet or another wired or wireless connection).

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A device for detecting particulate matter, comprising:
a laser, a reflector, an ellipsoidal reflector, and a detector, wherein:
the laser is configured to emit a beam;
the reflector is positioned on an optical axis between the detector and the ellipsoidal reflector and configured to reflect the beam toward the ellipsoidal reflector; and
the ellipsoidal reflector has a first focal region located on a path of the reflected beam on the optical axis, and a second focal region located on the optical axis at a surface of the detector.

2. The device of claim 1, wherein light scattered in the first focal region is reflected by the ellipsoidal reflector to the second focal region.

3. The device of claim 1, wherein the detector is configured to:
receive light reflected by the ellipsoidal reflector; and
determine a luminous intensity of the light reflected by the ellipsoidal reflector.

4. The device of claim 1, wherein the device includes a baffle positioned to block light reflected by the ellipsoidal reflector outside of the first focal region from reaching the detector.

5. A device for detecting particulate matter, comprising:
a first end and a second end opposing the first end, wherein the first and second ends are on an optical axis;
a laser;
a reflector;
an ellipsoidal reflector;
a baffle; and
a detector, wherein:
the reflector is positioned on the optical axis between the detector and the ellipsoidal reflector and angled with respect to the optical axis;
the laser is configured to emit a beam in a direction substantially perpendicular to the optical axis such that the beam is reflected by the reflector towards the ellipsoidal reflector;
the ellipsoidal reflector is positioned on the optical axis at the second end and includes a first focal region located on a path of the reflected beam and a second focal region located proximal to a surface of the detector, wherein light scattered in the first focal region is reflected by the ellipsoidal reflector to the detector;
the detector is positioned on the optical axis at the first end; and the baffle is positioned between the first end and the second end and to prevent light scattered outside of the first focal region from being received by the detector.

6. The device of claim 5, wherein the ellipsoidal mirror includes a surface defining an opening configured to allow the beam reflected by the reflector to pass therethrough.

7. The device of claim 6, wherein the system includes a beam dump at the second end configured to receive the beam reflected by the reflector.

8. The device of claim 6, wherein the opening is substantially centered on the ellipsoidal reflector.

9. The device of claim 5, wherein the system includes a flow sheath between the reflector and the ellipsoidal reflector and substantially perpendicular to the optical axis.

10. The device of claim 9, wherein the flow sheath includes an opening to allow the light scattered in the first focal region to pass therethrough.

11. The device of claim 5, wherein the light scattered in the first focal region is reflected by the ellipsoidal reflector and received by the detector in a particular angle range.

12. The device of claim 11, wherein, the angle range is between 25 degrees and 35 degrees from the optical axis.

13. The device of claim 5, wherein the device includes a first assembly and a second assembly, and wherein the first assembly includes the ellipsoidal reflector, and the second assembly includes the laser, the reflector, and the baffle.

14. The device of claim 13, wherein the first and second assemblies are securable to one another.

15. The device of claim 14, wherein the first and second assemblies are securable to one another by a sliding joint along the optical axis.

16. A method for detecting particulate matter, comprising:
emitting a beam of light from a laser;
directing the light towards an ellipsoidal reflector having a first focal region located on a path of the reflected light between the ellipsoidal reflector and a detector;
reflecting a scattered portion of the light by the ellipsoidal reflector towards the detector, the scattered portion scattered by airborne particulate matter traveling through the first focal region; and
receiving the reflected scattered portion of the light by a detector located at a second focal region of the ellipsoidal reflector, wherein the first focal region, the ellipsoidal reflector, the second focal region, and the detector are each on an optical axis.

17. The method of claim 16, wherein the method includes drawing the particulate matter through the first focal region using a fan.

18. The method of claim 16, wherein the method includes passing the particulate matter through the first focal region in a flow sheath.

19. The method of claim 16, wherein the method includes blocking another scattered portion from being received by the detector using a baffle, and wherein the other scattered portion is scattered by particulate matter outside the first focal region.

20. The method of claim 16, wherein the method includes determining a mass concentration of the particulate matter based on an intensity of the reflected scattered portion of the light received by the detector.

* * * * *